US011643437B2

(12) United States Patent
Yu et al.

(10) Patent No.: US 11,643,437 B2
(45) Date of Patent: May 9, 2023

(54) TANDEM REPEAT CANCER-TARGETING PEPTIDES FOR MOLECULAR CONJUGATION OR ENGINEERING AND USES THEREOF IN CANCER THERANOSTICS

(71) Applicant: Chang Gung Memorial Hospital, Taoyuan (TW)

(72) Inventors: John Yu, La Jolla, CA (US); Alice Yu, La Jolla, CA (US); Sheng-Hung Wang, Taipei (TW)

(73) Assignee: Chang Gung Memorial Hospital, Taoyuan (TW)

( * ) Notice: Subject to any disclaimer, the term of this patent is extended or adjusted under 35 U.S.C. 154(b) by 148 days.

(21) Appl. No.: 17/173,917

(22) Filed: Feb. 11, 2021

(65) Prior Publication Data

US 2021/0253636 A1 Aug. 19, 2021

Related U.S. Application Data

(60) Provisional application No. 62/976,811, filed on Feb. 14, 2020.

(51) Int. Cl.
| | |
|---|---|
| *C07K 7/06* | (2006.01) |
| *A61K 38/08* | (2019.01) |
| *A61K 47/69* | (2017.01) |
| *A61K 47/60* | (2017.01) |
| *C07K 16/32* | (2006.01) |
| *A61K 51/08* | (2006.01) |
| *C07K 7/08* | (2006.01) |
| *A61K 38/10* | (2006.01) |
| *A61K 39/395* | (2006.01) |
| *A61P 35/00* | (2006.01) |
| *A61K 31/353* | (2006.01) |

(52) U.S. Cl.
CPC ............. *C07K 7/06* (2013.01); *A61K 31/353* (2013.01); *A61K 38/08* (2013.01); *A61K 38/10* (2013.01); *A61K 39/39558* (2013.01); *A61K 47/60* (2017.08); *A61K 47/6907* (2017.08); *A61K 51/08* (2013.01); *A61P 35/00* (2018.01); *C07K 7/08* (2013.01); *C07K 16/32* (2013.01); *C07K 2317/31* (2013.01)

(58) Field of Classification Search
None
See application file for complete search history.

(56) References Cited

U.S. PATENT DOCUMENTS

| | | |
|---|---|---|
| 7,504,490 B1 | 3/2009 | Weinstock et al. |
| 8,961,971 B2 | 2/2015 | Hsu et al. |
| 10,052,307 B2 | 8/2018 | Kurisawa et al. |
| 2007/0032413 A1* | 2/2007 | Rosen .................... C07K 14/47 514/6.9 |
| 2011/0167514 A1 | 7/2011 | Brover et al. |
| 2013/0142867 A1 | 6/2013 | Yu et al. |

FOREIGN PATENT DOCUMENTS

| | | |
|---|---|---|
| WO | WO-00/56755 A1 | 9/2000 |
| WO | WO-2019/086627 A1 | 5/2019 |

OTHER PUBLICATIONS

Sequence entry 4325 for US 2007/0032413 (retrieved from http://seqdata.uspto.gov/?pageRequest=docDetail&DocID=U.S. Pat. No. 20070032413A1 on Oct. 31, 2022, 1 page). (Year: 2022).*
Banerjee et al "Clinical Applications of Gallium-68" Applied Radiation and Isotopes vol. 76, pp. 2-13, 2013.
Arap et al "Cell Surface Expression of the Stress Response Chaperone GRP78 Enables Tumor Targeting by Circulating Ligands" Cancer Cell vol. 6, pp. 275-284, 2004.
Cao et al "Angiogenesis Inhibited by Drinking Tea" Nature vol. 398, p. 381, 1999.
Chung et al "Self-Assembled Micellar Nanocomplexes Comprising Green Tea Catechin Derivatives and Protein Drugs for Cancer Therapy" Nature Nanotechnology vol. 9, pp. 907-912, 2014.
Du et al. "Epigallocatechin Gallate (EGCG) is the Most Effective Cancer Chemopreventive Polyphenol in Green Tea" Nutrients vol. 4, pp. 1679-1691, 2012.
Jakobsen et al "Phage Display-Derived Human Monoclonal Antibodies Isolated by Binding to the Surface of Live Primary Breast Cancer Cells Recognize GRP78" Cancer Research vol. 67, pp. 9507-9517, 2007.
Jankun et al "Why Drinking Green Tea Could Prevent Cancer" Nature vol. 387, p. 561, 1997.
LEE "Glucose Regulated Proteins in Cancer: Molecular Mechanisms and Therapeutic Potential" Nature Reviews Cancer vol. 14, pp. 263-276, 2014.
Lee et al "A Novel Peptide Specifically Binding to Nasopharyngeal Carcinoma for Targeted Drug Delivery" Cancer Research vol. 64, pp. 8002-8008, 2004.
Lee et al "A Novel Peptide That Directs Chemotherapy Against Breast Cancer Stem Cell" The FASEB Journal vol. 29, S1, 2015.

(Continued)

*Primary Examiner* — Ronald T Niebauer
(74) *Attorney, Agent, or Firm* — Cesari & McKenna, LLP

(57) ABSTRACT

An isolated cancer-targeting peptide that includes at least two copies of the amino acid sequence PFLP (SEQ ID NO: 1) or PFLF (SEQ ID NO: 2). Also disclosed is a pharmaceutical composition for treating cancer. The composition contains the isolated cancer-targeting peptide and an anti-cancer agent. Further disclosed is a bispecific anti-cancer antibody that includes the isolated cancer-targeting peptide and an antigen-binding peptide that stimulates T cell activity. Methods are provided for treating cancer by administering the pharmaceutical composition or the bispecific anti-cancer antibody. Further provided is a method for diagnosing cancer by administering a radionuclide-labeled cancer-targeting peptide to an individual and imaging a location of the radionuclide.

11 Claims, 4 Drawing Sheets

Specification includes a Sequence Listing.

(56) References Cited

OTHER PUBLICATIONS

Liu et al "Monoclonal Antibody Against Cell Surface GRP78 as a Novel Agent in Suppressing PI3K/AKT Signaling, Tumor Growth and Metastasis" Clinical Cancer Research vol. 19, pp. 6802-6811, 2013.
Mintz et al "Fingerprinting the Circulating Repertoire of Antibodies from Cancer Patients" Nature Technology vol. 21, pp. 57-63, 2003.
Rasche et al "The Natural Human IgM Antibody PAT-SM6 Induces Apoptosis in Primary Human Multiple Myeloma Cells by Targeting Heat Shock Protein GRP78" PLOS ONE vol. 8, pp. 1-11, 2013.
Wang et al "Structure-Based Optimization of GRP78-Binding Peptides That Enhances Efficacy in Cancer Imaging and Therapy" Biomaterials vol. 94, pp. 31-44, 2016.
Lee et al "A Novel Peptide Directs Chemotherapy Against Breast Cancer Stem Cells" Abstract No. 5462, Poster Board No. D191, presented at FASEB Mar. 28-Apr. 1, 2015.

* cited by examiner

TANDEM REPEAT CANCER-TARGETING PEPTIDES FOR MOLECULAR CONJUGATION OR ENGINEERING AND USES THEREOF IN CANCER THERANOSTICS

CROSS-REFERENCE TO RELATED APPLICATIONS

The present application claims the benefit of U.S. Provisional Patent Application Ser. No. 62/976,811 filed on Feb. 14, 2020, the content of which is hereby incorporated by reference in its entirety.

BACKGROUND

Recurrence of cancer is a major clinical challenge. Cancer stem cells, which exist as a subpopulation in a tumor, are particularly resistant to chemotherapy drugs and radiation. See Lee et al., 2015, FASEB J. 29:Supplement 629.18. After conventional chemotherapy, an elevated proportion of cancer stem cells in tumors is an important predictive factor for cancer recurrence. See Lee et al.

It has been reported that Glucose regulated protein of 78 kDa (GRP78), a member of the HSP70 protein family, is found on the surface of a variety of cancer cells but not on normal cells. See Wang et al., 2016, Biomaterials 94:31-44 and Liu et al. 2013, Clin. Cancer Res. 19:6802-11. GRP78 has also been implicated in both cancer cell drug resistance and stem-like cell behaviors, and has further been shown to be a targetable cell surface receptor. See Bachelder, 2018. GRP78 is thus an attractive target for anti-cancer therapies that should reduce damage to normal cells and reduce recurrence.

Cancer-targeting peptides (CTPs) that bind specifically to GRP78 have been previously identified. See Wang et al. The CTPs were found to interact with a peptide-binding domain (PBD) of GRP78 in a linear-peptide conformation. These CTPs, when conjugated to the chemotherapy drug doxorubicin, have been shown to enhance the anti-tumor efficacy of this drug, and also target both cancer cells and cancer-stem cells, thereby reducing the recurrence rates of cancer. See Liu et al.

There is a need to develop CTPs having higher affinity for cancer stem cells and to develop anti-cancer treatment modalities based on the CTPs.

SUMMARY

To meet this need, an isolated cancer-targeting peptide is disclosed that includes at least two copies of the amino acid sequence PFLP (SEQ ID NO: 1) or PFLF (SEQ ID NO: 2).

Also disclosed herein is a pharmaceutical composition for treating cancer. The composition contains the isolated cancer-targeting peptide and an anti-cancer agent.

Further, a bispecific anti-cancer antibody is disclosed. This antibody includes the isolated cancer-targeting peptide and an antigen-binding peptide that stimulates T cell activity.

Moreover, methods for treating cancer by administering the pharmaceutical composition or the bispecific anti-cancer antibody are both within the scope of the invention.

Another method is disclosed for diagnosing cancer. The method is carried out by administering an individual a radionuclide-labeled cancer-targeting peptide that contains at least two copies of the amino acid sequence PFLP (SEQ ID NO: 1) or PFLF (SEQ ID NO: 2) and subjecting the individual to an imaging technique to determine a location and an amount of the radionuclide-labeled cancer-targeting peptide.

The details of several embodiments of the present invention are set forth in both the description and the drawings below. All features, objects, and advantages of the invention will be apparent from the description and the drawings, as well as from the appended claims.

BRIEF DESCRIPTION OF THE DRAWINGS

The description below refers to the accompanying drawings, of which.

DETAILED DESCRIPTION

Figure 1:
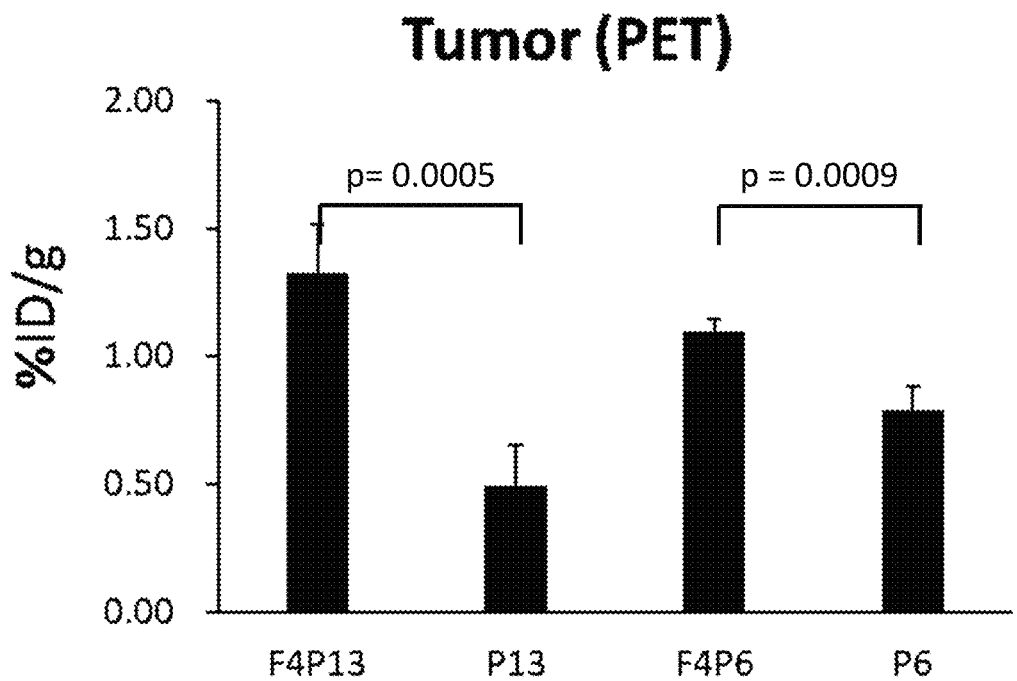
FIG. 1 is a bar graph showing, for each of the four indicated radio-labelled peptides, the percent injected dose per g (% ID/g) determined by positron emission tomography (PET) analysis after injection into tumor-bearing mice. Peptide sequences are shown in Table 1 below.

As summarized above, an isolated cancer-targeting peptide is provided that includes at least two copies of the amino acid sequence PFLP (SEQ ID NO: 1).

The two copies of PFLP in the cancer-targeting peptide can overlap with each other. For example, the cancer-targeting peptide can be RPFLPFLPY (SEQ ID NO: 5) and RPFLPFLPYRPFLPFLPY (SEQ ID NO: 6).

Another isolated cancer-targeting peptide includes at least two copies of PFLF (SEQ ID NO: 2). Examples of this peptide include RPFLFPFLFY (SEQ ID NO: 7) and RPFLFPFLFYRPFLFPFLFY (SEQ ID NO: 8).

The above-described cancer-targeting peptides can specifically bind to GRP-78 on cancer cells. In other words, no additional amino acids are required. As such, encompassed by the invention are any of the above cancer-targeting peptides that are free of the sequence RLLDT (SEQ ID NO: 15).

Also within the scope of the invention is a cancer-treating pharmaceutical composition that includes any of the above-described isolated cancer-targeting peptides and an anti-cancer agent.

In certain compositions, the anti-cancer agent is a monoclonal antibody, e.g., anti-HER2/neu, anti-PD-1, anti-PD-L1, or anti-CTLA4.

In other compositions the anti-cancer agent is a chemotherapy agent, e.g., doxorubicin, vincristine, vinorelbine, paclitaxel, or irinotecan.

Further, the anti-cancer agent in the pharmaceutical composition can include a radioisotope, e.g., $^{90}Y$, $^{125}I$, $^{188}Re$, $^{68}Ga$, $^{111}In$, or $^{131}I$. In a specific example, the radioisotope is chelated by a chelating agent that is conjugated to the cancer-targeting peptide.

Referring back to the cancer-treating pharmaceutical composition, a particular example includes a micellar nano-complex (MNC) having a core encapsulating the anti-cancer agent and a shell that includes the isolated cancer-targeting peptide.

The core can be, e.g., a monoclonal antibody complexed with oligomeric epigallocatechin-3-O-gallate (EGCG). In a specific composition, the monoclonal antibody is an anti-HER2/neu antibody, e.g., trastuzumab.

The shell can be formed of a conjugate of EGCG and polyethylene glycol (PEG) to which the cancer-targeting peptide is attached, e.g., to the PEG. The shell can further include a PEG/EGCG conjugate that is free of the cancer-targeting peptide.

Alternatively, the shell can be a liposome formed of distearoylphosphatidyl-choline, cholesterol, and PEG-distearoylphosphoethanolamine. Polymers such as poly(lactic-co-glycolic acid) and polyvinylchloride can also be used as a component of the shell.

The scope of the invention also encompasses a bispecific anti-cancer antibody that includes any of the isolated cancer-targeting peptides described above and an antigen-binding peptide that stimulates T cell activity. Exemplary antigen-binding peptides specifically bind to CD3, PD-1, CTLA-4, LAG-3, TIM-3, TIGIT, VISTA, B7-H3, OX40, GITR, ICOS, or 41BB. The antigen-binding peptides can be, e.g., a single chain Fv (scFv) or a single-domain antibody. In an exemplary bispecific anti-cancer antibody, the antigen-binding peptide is an anti-CD3 scFv. A specific example of the bispecific anti-cancer antibody is a heterodimer consisting of SEQ ID NO: 12 and SEQ ID NO: 14.

Methods for treating cancer are provided that take advantage of the cancer-targeting properties of the pharmaceutical compositions and bispecific anti-cancer antibodies set forth supra.

For example, one method for treating cancer is carried out by administering to a cancer patient the pharmaceutical composition described above that includes a cancer-targeting peptide and an anti-cancer agent. In a specific method, cancer is treated by administering a MNC having a core of oligomeric EGCG complexed with trastuzumab and a shell that contains (i) the cancer-targeting peptide attached to a PEG-EGCG conjugate and (ii) a PEG-EGCG conjugate lacking the peptide.

A distinct method for treating cancer is accomplished by administering the bispecific anti-cancer antibody described above to a cancer patient. In one example, the bispecific anti-cancer antibody is a heterodimer consisting of SEQ ID NO: 12 and SEQ ID NO: 14.

The cancers that can be treated by the above methods include, but are not limited to, breast cancer, hepatocellular carcinoma, prostate cancer, lung cancer, ovarian cancer, kidney cancer, uterine cancer, cervical cancer, melanoma, embryonal carcinoma, leukemia, and osteosarcoma.

Mentioned above is a method for diagnosing cancer using a radionuclide-labeled cancer-targeting peptide that contains at least two copies of the amino acid sequence SEQ ID NO: 1 or SEQ ID NO: 2. The radionuclide-labeled cancer-targeting peptide can have the amino acid sequence of SEQ ID NOs: 5, 6, 7, or 8.

To accomplish the method, the radionuclide-labeled cancer-targeting peptide is administered to, e.g., injected into, an individual suspected of having cancer. The individual is then subjected to an imaging technique, such as positron emission tomography, to quantify the amount of the radionuclide-labeled cancer-targeting peptide that accumulated in various body tissues. Cancer is diagnosed if the quantity of the radionuclide-labeled cancer-targeting peptide accumulated in a localized area of a tissue is greater than the background level in neighboring areas of the tissue.

In a specific method, a cancer-targeting peptide having the amino acid sequence of SEQ ID NO: 6 is labeled with radionuclide $^{68}Ga$ and administered to the individual.

Without further elaboration, it is believed that one skilled in the art can, based on the disclosure herein, utilize the present disclosure to its fullest extent. The following specific examples are, therefore, to be construed as merely descriptive, and not limitative of the remainder of the disclosure in any way whatsoever. All publications and patent documents cited herein are incorporated by reference in their entirety.

EXAMPLES

Example 1: Tandem-Repeat Cancer Targeting Peptides (TR-CTPs)

TR-CTPs were designed that included at least one tandem repeat of a binding motif, i.e., $PFLX_1$ (where X1 is P or F) found in CTPs previously described in U.S. Pat. No. 8,846,623. The peptide sequences are shown in Table 1 below, with the repeat sequences underlined and bolded. Note that in F4P6-TR-CTP and F5P6-TR-CTP, the repeat sequences overlap by one amino acid.

Not to be bound by theory, it is believed that the increased length of TR-CTP as compared to CTPs will prevent steric hindrance when incorporated into a bi-specific antibody. Further, repeats of binding motifs should increase binding affinity. Moreover, the novel TR-CTPs described herein with repeats should be suitable for conjugation at either its N-terminus or its C-terminus.

TABLE 1

Amino acid sequences of TR-CTPs and CTPs

| CTP | SEQUENCE | SEQ ID NO |
|---|---|---|
| P6-CTP | RLLDTNRPFLPY | 3 |
| F4P6-TR-CTP | RPFLPFLPY | 5 |
| F5P6-TR-CTP | RPFLPFLPYRPFLPFLPY | 6 |
| P13-CTP | RLLDTNRPFLFY | 4 |
| F4P13-TR-CTP | RPFLFPFLFY | 7 |
| F5P13-TR-CTP | RPFLFPFLFYRPFLFPFLFY | 8 |

Example 2: Binding Affinities of N-Terminal Extended TR-CTPs

Biotin-labeled TR-CTPs and CTPs were synthesized (Biotools Co., Ltd, Taiwan) to evaluate kinetics of binding to GRP78 by surface plasmon resonance. TR-CTPs and CTPs were extended by five amino acids (GGGGS; SEQ ID NO: 9) at their N-termini. The N-termini were labeled with a single biotin molecule per TR-CTP/CTP through an aminohexanoic acid linkage.

Also biotin labeled were two negative control peptides, in which the L-Leu residues within the sequences of F4P6-TR-CTP and F4P13-TR-CTP were replaced with D-Leu residues (dF4P6 and dF4P13, respectively).

Streptavidin was immobilized to a sensor chip (CMS; GE Healthcare) having a matrix of carboxymethylated dextran covalently attached to a gold surface using a standard amine-coupling method according to established procedures (GE Healthcare). The biotin-labeled TR-CTPs were immobilized on the chip by flowing them over the chip at a flow rate of 5 μl/min using HBS-P+ (GE Healthcare) as the running buffer.

The binding affinities of various concentrations (~0.1-15 μM) of the peptide-binding domain of GRP78 (GRP78-PBD, amino acids 421-639) to the chip-bound TR-CTPs and CTPs were then analyzed using a BIACORE™ T200 instrument (GE Healthcare). Sensor chips were regenerated by washing the chip surface for 30 s with glycine buffer (10 mM; pH 11.5). Chips were reused after two chip regeneration cycles followed by a 120 s wash with running buffer. The results are shown in Table 2 below.

TABLE 2

Binding affinity of GRP78-PBD for N-conjugated CTPs and TR-CTPs

| Biotin-CTP | Association rate $K_{on}$ (M$^{-1}$S$^{-1}$) | Dissociation rate $K_{off}$ (S$^{-1}$) | Dissociation constant $K_D$ (M) |
|---|---|---|---|
| P6-CTP | 1.5 × 10$^3$ | 3.0 × 10$^{-3}$ | 1.9 × 10$^{-6}$ |
| F4P6-TR-CTP | 2.3 × 10$^3$ | 2.8 × 10$^{-3}$ | 1.2 × 10$^{-6}$ |
| F5P6-TR-CTP | 8.9 × 10$^2$ | 9.1 × 10$^{-4}$ | 1.0 × 10$^{-6}$ |
| P13-CTP | 1.2 × 10$^3$ | 3.4 × 10$^{-3}$ | 2.7 × 10$^{-6}$ |
| F4P13-TR-CTP | 7.9 × 10$^2$ | 1.7 × 10$^{-3}$ | 2.1 × 10$^{-6}$ |
| F5P13-TR-CTP | 1.9 × 10$^3$ | 1.2 × 10$^{-3}$ | 6.1 × 10$^{-7}$ |
| dF4P6 | N.B.$^a$ | N.B. | N.B. |
| dF4P13 | N.B. | N.B. | N.B. |

$^a$ = No binding signal detected

The dissociation constants ($K_D$) for P6 series peptides (repeat sequence PFLP) P6-CTP (one copy), F4P6-TR-CTP (two copies), and F5P6-TR-CTP (four copies) were 1.9× 10$^{-6}$M, 1.2×10$^{-6}$M, and 1.0×10$^{-6}$M, respectively. The increase in binding affinities, i.e. decrease in $K_D$, correlated with an increase in the number of copies of the binding sequence present in the TR-CTP peptide.

Similar results were found for the P13 series peptides (repeat sequence PFLF). The $K_D$ values for P13-CTP (one copy), F4P13-TR-CTP (two copies), and F5P13-TR-CTP (four copies) were 2.7×10$^{-6}$M, 2.1×10$^{-6}$M, and 6.1×10$^{-7}$M. Among all peptides tested, the F5P13-TR-CTP demonstrated the highest binding affinity for the peptide binding domain of GRP78.

The dissociation rate ($K_{off}$) reflects the binding stability of TR-CTP/GRP78-PBD complexes. The smaller the $K_{off}$ value the slower the dissociation rate, i.e., the greater the stability of the complex. As shown in Table 2, the $K_{off}$ values for P6-CTP, F4P6-TR-CTP, and F5P6-TR-CTP were 3.0×10$^{-3}$ S$^{-1}$, 2.8×10$^{-3}$ S$^{-1}$, and 9.1×10$^{-4}$ S$^{-1}$, respectively. The $K_{off}$ values for P13-CTP, F4P13-TR-CTP, and F5P13-TR-CTP were 3.4×10$^{-3}$ S$^{-1}$, 1.7×10$^{-3}$ S$^{-1}$, and 1.2×10$^{-3}$ S$^{-1}$, respectively. A general correlation was seen between the number of repeat sequences in the TR-CTP and the dissociation rates.

As expected, the two D-Leu-substituted negative control peptides, i.e., dF4P6 and dF4P13, showed negligible binding to GRP78-PBD; their $K_D$ values could not be determined. See Table 2, last two rows.

Example 3: Binding Affinities of C-Terminal Extended TR-CTPs

The P13-series peptides described above in Example 1 were also biotin labeled after extending them at their C-termini with the sequence GGGGSK (SEQ ID NO: 10). Biotin was conjugated to the C-terminal lysine residue using standard techniques. Binding affinities of GRP78-PBD for the sensor chip-bound peptides were determined as described above in Example 2. The results are shown in Table 3 below.

TABLE 3

Kinetics of GRP78-PBD binding to C-conjugated CTPs and TR-CTPs.

| CTP-cBiotin | Association rate $K_{on}$ (M$^{-1}$S$^{-1}$) | Dissociation rate $K_{off}$ (S$^{-1}$) | Dissociation constant $K_D$ (M) |
|---|---|---|---|
| P13-CTP | 9.7 × 10$^2$ | 2.0 × 10$^{-3}$ | 2.7 × 10$^{-6}$ |
| F4P13-TR-CTP | 1.8 × 10$^3$ | 1.2 × 10$^{-3}$ | 6.6 × 10$^{-7}$ |
| MF4P13-TR-CTP | 2.4 × 10$^2$ | 2.9 × 10$^{-4}$ | 1.2 × 10$^{-6}$ |

The binding affinities of GRP78-PBD to the C-terminal biotinylated peptides were similar to the affinities to their N-terminally labeled counterparts. Further, the binding affinities ($K_D$) and dissociation rates ($K_{off}$) of F4P13-TR-CTP with C-terminal biotin and MF4P13-TR-CTP-cBiotin, both having 2 copies of PFLF, were all better than that of P13-CTP-cBiotin, having only one copy. Peptide MF4P13-TR-CTP has the same amino acid sequence as F4P13-TR-CTP with the addition of methionine at its N-terminus.

Example 4. In Vivo Tumor Targeting by TR-CTPs

The ability of TR-CTPs to target tumor cells in vivo was tested in N87 tumor-bearing mice, a HER2-positive gastric cancer xenograft model. N87 tumors were established in NOD SCID gamma (NSG) mice using standard protocols. In brief, tumors were established by injecting the NSG mice subcutaneously with 3×10$^{-6}$ N87 cells per animal. Tumors were allowed to grow to a volume of 100-200 mm$^3$ prior to performing the treatments described below.

Four peptides, i.e., F4P13-TR-CTP, P13-CTP, F4P6-TR-CTP, and P6-CTP were labeled with $^{68}$Ga using standard techniques. In brief, dodecane tetraacetic acid polyethylene glycol (DOTA-PEG3350) was conjugated to each peptide to form DOTA-CTP-PEG3350 (Mission Biotech, Taipei, Taiwan). Each DOTA-CTP-PEG3350 was mixed with $^{68}$GaCl$_3$ (itG, Germany) in 0.1 M sodium acetate buffer (pH 5.5) and incubated at 95° C. for 10 minutes. The $^{68}$Ga-DOTA-CTP-PEG3350 were used directly without further purification.

More specifically, a 250 μCi dose of each of the four $^{68}$Ga-labeled peptides mentioned above was separately injected intravenously into four NSG mice. Fifteen minutes post-injection, each mouse was scanned for 15 min. using a nanoScan PET/CT (Mediso Pacific) and static microPET images of tumors were obtained. Quantification of the images can be seen in FIG. 1. The results showed that the percent injected dose per gram (% ID/g) in the tumors after administration of F4P13-TR-CTP and F4P6-TR-CTP was significantly higher, as compared to P13-CTP and P6-CTP, respectively. Clearly, the presence of tandem repeats of the binding sequences, i.e., PFLF and PFLP, improved tumor targeting of the CTPs.

Figure 2:
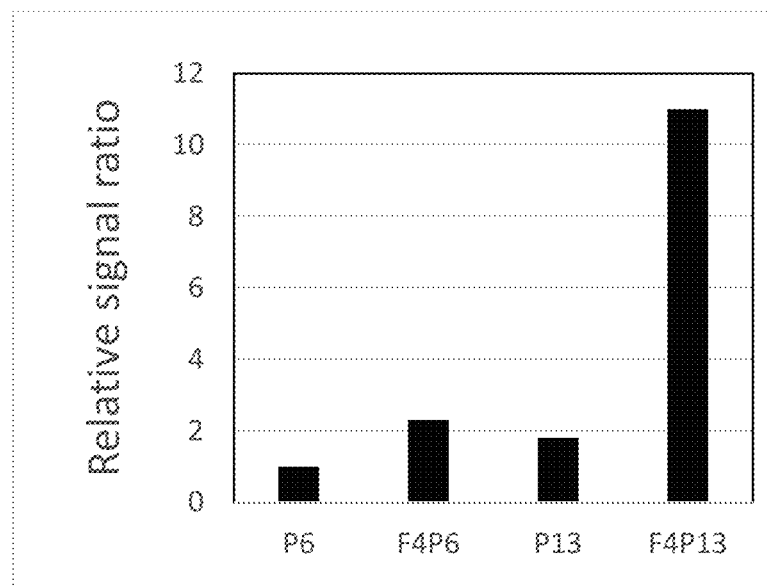
FIG. 2 is a bar graph showing relative signal ratio in tumor tissue sections of tumor-bearing mice injected with radiolabeled peptides P6, F4P6, P13 or F4P13.

The PET studies were confirmed by autoradiographic studies of cryo-sectioned tumor tissue excised from the injected mice. The distribution pattern of all four $^{68}$Ga-conjugated peptides was uneven throughout the tumors. Quantification of radiographic signals in tumor sections is shown in FIG. 2. Radiographic signals in $^{68}$Ga-F4P6-TR-CTP and $^{68}$Ga-F4P13-TR-CTP-injected mice were higher relative to those of $^{68}$Ga-P6-CTP and $^{68}$Ga-P13-CTP-injected mice, respectively, in tumor tissue, indicating that the tandem repeat peptides, i.e., TR-CTPs, can better target cancer, as compared to CTPs. In particular, relative to the radiographic signal from $^{68}$Ga-P6-CTP, set at 1, the radiographic signal of $^{68}$Ga-P13-CTP, $^{68}$Ga-F4P6-TR-CTP, and $^{68}$Ga-F4P13-TR-CTP was 1.8, 2.3, and 11, respectively.

Example 5. Bispecific Antibodies

Figure 3:
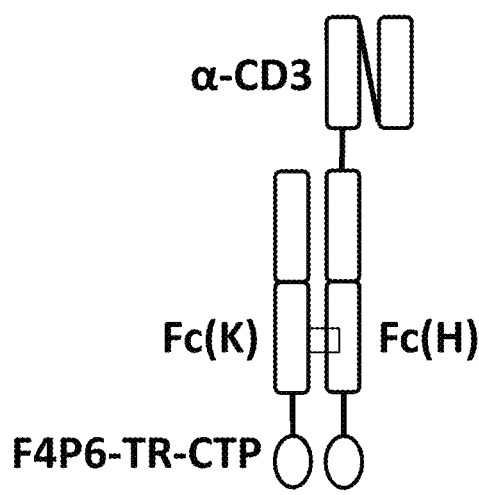
FIG. 3 is a diagram of a bispecific anti-cancer antibody construct of the invention. α-CD3=anti-CD3 scFv, Fc(K)= heavy chain with knob dimerization sequence, Fc(H) heavy chain with hole dimerization sequence, F4P6-TR-CTP=F4P6 tandem repeat cancer-targeting peptide that binds to GRP-78.

A bispecific antibody-like protein was engineered to evaluate the suitability of TR-CTPs for immunotherapy, taking advantage of the so-called "knob-and-hole" technology for high efficiency formation of heterodimers. See, e.g., U.S. Pat. No. 8,961,971. Briefly, an F4P6-TR-CTP was fused separately to the C-terminus of an Fc-hole peptide and to the C-terminus of an Fc-knob peptide. An anti-CD3 scFv was fused to the N-terminus of the Fc-hole peptide. The bispecific antibody-like construct, designated as F4P6-BsAb, is shown schematically in FIG. 3. In this example, the F4P6-TR-CTP Fc-hole fusion has the amino acid sequence of SEQ ID NO: 12 and the F4P6-TR-CTP Fc-knob fusion has the amino acid sequence of SEQ ID NO: 14. A control antibody, i.e., Ctrl-BsAb, lacked the F4P6-TR-CTP sequence.

Following expression and purification of F4P6-BsAb, the kinetics of GRP78-PDB binding to it was evaluated by surface plasmon resonance as described in Example 1 above, differing in that the F4P6-BsAb was directly coupled to the CMS sensor chip by amine-coupling. The results showed that GRP78-PBD had a $K_D$ value of $1.1 \times 10^{-6}$ M and a $K_{off}$ value of $9.4 \times 10^{-4}$ S$^{-1}$ for F4P6-BsAb, values close to those of GRP78-PBD for the isolated peptide F4P6-TR-CTP (see Table 2).

Example 6. Killing of Cancer Cells Induced by F4P6-BsAb

The ability of bispecific antibody-like construct F4P6-BsAb to induce cell killing by peripheral blood mononuclear cells (PBMC) was tested on TOV21G ovarian cancer target cells and N87 gastric cancer target cells.

Figure 4A:
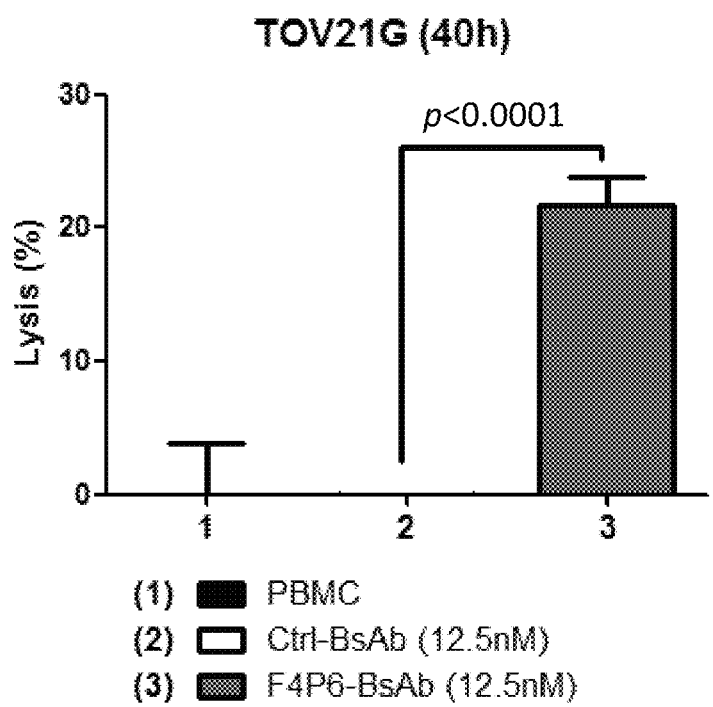
FIG. 4A is a bar graph showing percent lysis (Lysis %) of TOV21G ovarian cancer cells after 40 h incubation with PBMC effector cells in the absence (PBMC) or presence (Ctrl-BsAb and F4P6-BsAb) of bispecific antibodies at the indicated concentration.
Figure 4B:
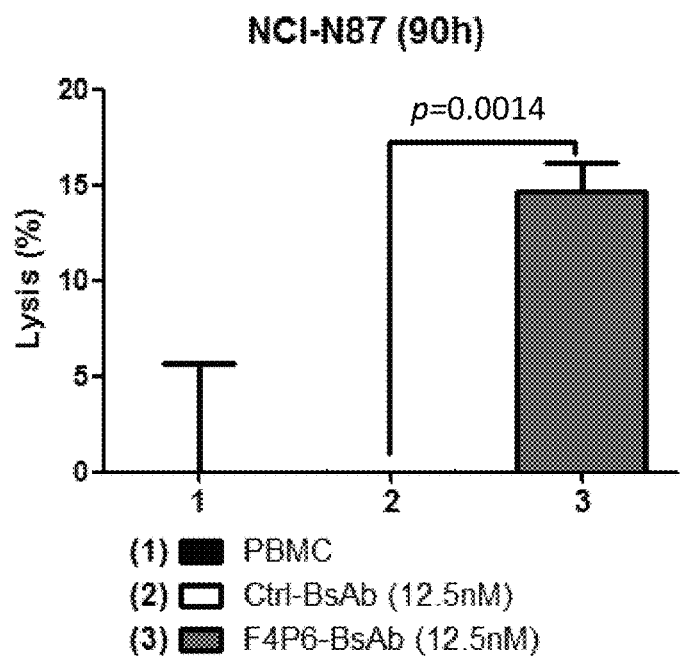
FIG. 4B is a bar graph showing percent lysis (Lysis %) of NCI-N87 gastric cancer cells after 90 h incubation with PBMC effector cells in the absence (PBMC) or presence (Ctrl-BsAb and F4P6-BsAb) of bispecific antibodies at the indicated concentration.

Target cells were seeded at $2 \times 10^4$ cells per well of a 96-well electronic microtiter plate ("E-plate"; ACEA Biosciences, Inc.) and allowed to adhere for 2 h. PBMC effector cells, PBMC effector cells plus F4P6-BsAb, and PBMC effector cells plus Ctrl-BsAb that lacks the P4P6-TC-CTP sequence were added to reach a final effector-to-target ratio of 10:1. The concentration of F4P6-BsAb and Ctrl-BsAb was 12.5 nM. Data was gathered and quantified using an xCELLigence Real-Time Cell Analysis system ("RTCA"; ACEA Biosciences, Inc.) as directed by the manufacturer. The results are shown in FIGS. 4A and 4B.

In the presence of F4P6-BsAb, PBMC mediated lysis of 22% and 15% of TOV21G cells (FIG. 4A) and N87 cells (FIG. 4B), respectively, while cell lysis in the absence of F4P6-BsAb or in the presence of Ctrl-BsAb was not detectable.

Example 7. TR-CTP Micellar Nanocomplexes

It is known that micellar nanocomplexes (MNC) having (i) a core formed of the anti-cancer monoclonal antibody trastuzumab (Herceptin®; anti-HER-2/neu mAb) and oligomerized epigallocatechin-3-O-gallate (oEGCG), and (ii) a shell formed of poly(ethylene glycol)-EGCG (PEG-EGCG) has better tumor selectivity, greater cancer cell growth inhibitory activity, and a longer blood half-life, as compared to free Herceptin. See, e.g., Chung et al., Nat. Nano-technol. 9:907-12.

An MNC was prepared to test the ability of a TR-CTP to improve MNC effectiveness. F4P6-TR-CTP was conjugated to PEG-EGCG to yield F4P6-TR-CTP-PEG-EGCG as follows. F4P6-TR-CTP was PEGylated using CHO-PEG-NHS with addition of N,N-Diisopropylethylamine in dimethylformamide. F4P6-TR-CTP-PEG-EGCG was synthesized by the Baeyer reaction between the aldehyde (CHO) group of the PEGylated F4P6-TR-CTP and the nucleophilic ring of EGCG. The resulting product were dialyzed (MWCO=3500) and lyophilized to give F4P6-TR-CTP-PEG-EGCG. See Chung et al.

Figure 5:
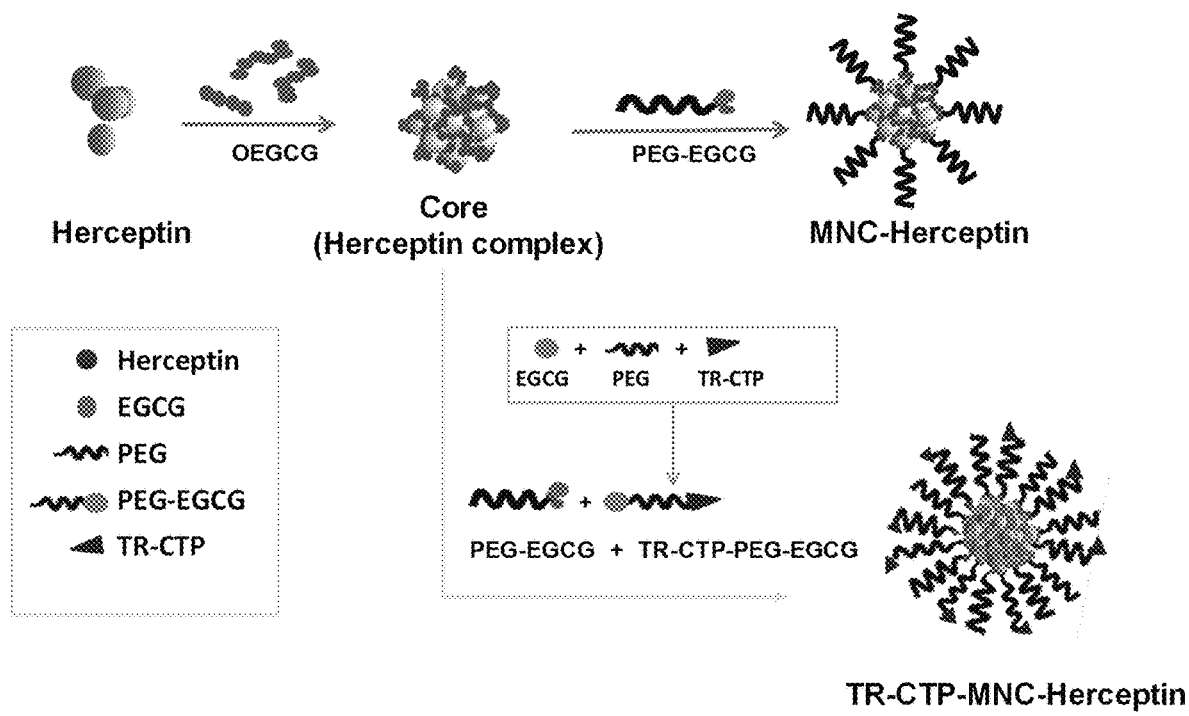
FIG. 5 schematically depicts anti-cancer micellar nanocomplexes (MNC). EGCG=epigallocatechin-3-O-gallate; oEGCG=oligomerized epigallocatechin-3-O-gallate; PEG=poly(ethylene glycol); TR-CTP=tandem repeat cancer-targeting peptide.

A Herceptin/oEGCG core was prepared as described previously. See Chung et al. MNC were prepared by mixing together the Herceptin/oEGCG core with either PEG-EGCG to form MNC-Herceptin or F4P6-TR-CTP-PEG-EGCG to form F4P6-MNC-Herceptin. The MNC are shown diagrammatically in FIG. 5.

Example 8. Cancer Cell Killing In Vitro by TR-CTP-MNC

Figure 6:
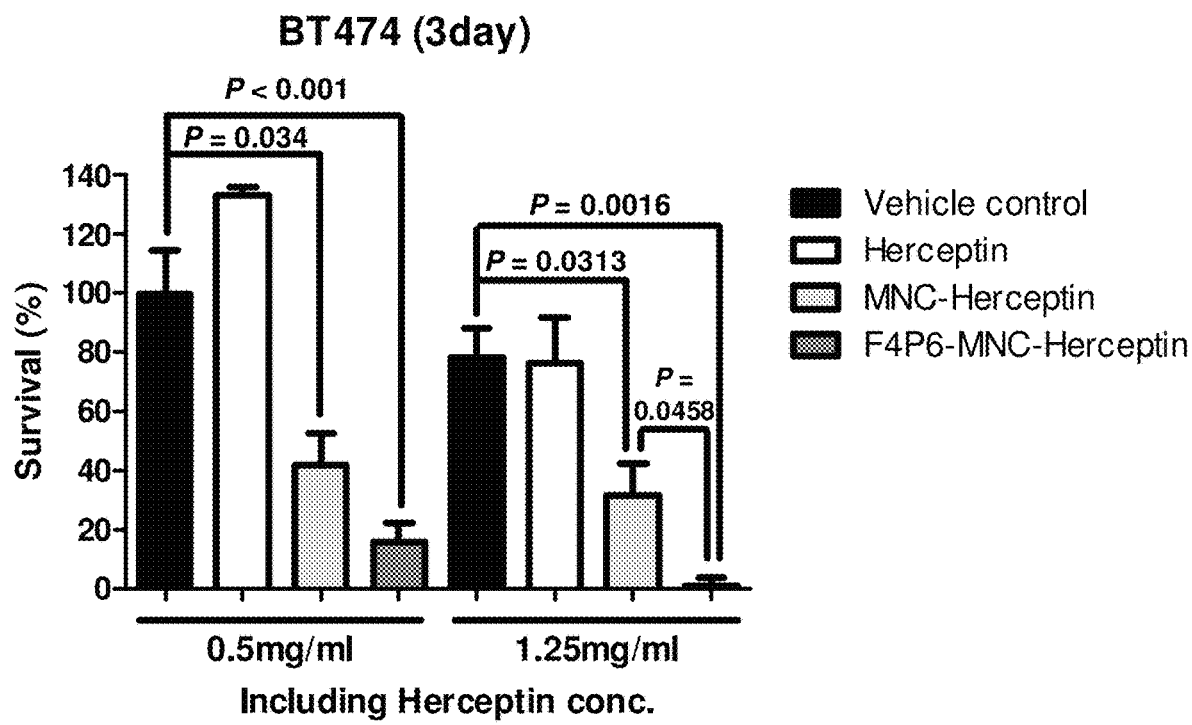
FIG. 6 is a bar graph showing percent survival of BT474 human breast carcinoma cells incubated with vehicle, Herceptin, MNC-Herceptin, or F4P6-MNC-Herceptin as indicated.

The ability of F4P6-TR-CTP-MNC-Herceptin to kill cancer cells was compared to that of MNC-Herceptin in HER-2/neu. Briefly, BT-474 human breast carcinoma cells, which overexpress HER2/neu, were seeded at $1 \times 10^4$ cells per well in a 96-well E-plate and cultured for one day. Wells were treated with vehicle, Herceptin alone, MNC-Herceptin, or F4P6-TR-CTP-MNC-Herceptin in amounts corresponding to 0.5 mg/ml and 1.25 mg/ml Herceptin. Cell viability was assessed after 3 days using RTCA as described in Example 6, supra. The results, expressed as percent survival, are shown in FIG. 6.

At the concentrations tested, Herceptin alone did not inhibit survival of BT-474 cells, as compared to vehicle control. MNC-Herceptin reduced cell survival to 30-40% at both tested concentrations, as compared to 100% survival for vehicle treated cells.

F4P6-MNC-Herceptin was more effective at killing BT-474 breast cancer cells compared to either Herceptin alone or MNC-Herceptin. Indeed, treatment of cells with F4P6-MNC-Herceptin at a concentration corresponding to 1.25 mg/ml Herceptin unexpectedly reduced their survival to only 1% of vehicle control. Clearly, TR-CTP enhanced the in vitro cell killing activity of MNC-Herceptin.

Example 9. Cancer Cell Killing In Vivo by TR-CTP-MNC

Figure 7:
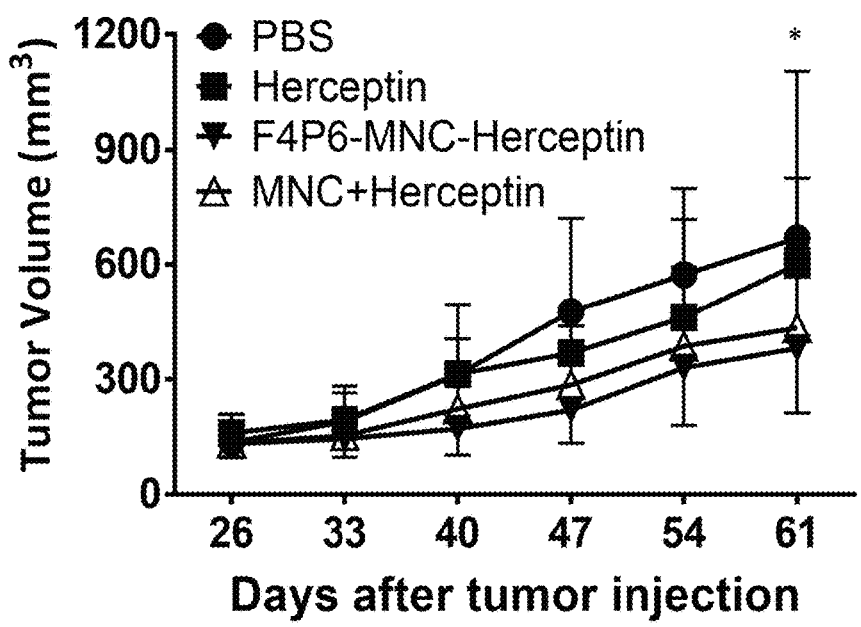
FIG. 7 is a plot of tumor volume versus days after injection into mice of N87 tumor cells. Mice were injected once weekly for 4 weeks with the indicated treatment. * p=0.041.

As Herceptin inhibits tumor growth, we sought to determine whether TR-CTP-MNC-Herceptin enhances the anti-cancer activity of Herceptin in vivo. N87 tumors were established as described above in Example 4. Mice bearing 100-200 mm$^3$ sized tumors were injected intravenously with 125 μg of either free Herceptin, MNC-Herceptin, or F4P6-MNC-Herceptin weekly for four weeks. The results are shown in FIG. 7.

F4P6-MNC-Herceptin inhibited tumor growth to a greater extent as compared to free Herceptin. Indeed, the tumor sizes in F4P6-MNC-Herceptin treated mice were significantly smaller than those in the Herceptin treated group 61 days after injection of tumor cells. See FIG. 7. Tumor growth inhibition mediated by F4P6-MNC-Herceptin was slightly greater than that mediated by MNC-Herceptin.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An isolated cancer-targeting peptide, having the amino acid sequence of RPFLFPFLFY (SEQ ID NO: 7) or RPFLFPFLFYRPFLFPFLFY (SEQ ID NO: 8).

2. A pharmaceutical composition for treating cancer, comprising the isolated cancer-targeting peptide of claim 1 and an anti-cancer agent.

3. The pharmaceutical composition of claim 2, further comprising a micellar nanocomplex having a core encapsulating the anti-cancer agent and a shell that includes the isolated cancer-targeting peptide.

4. The pharmaceutical composition of claim 3, wherein the isolated cancer-targeting peptide is conjugated to polyethylene glycol.

5. The pharmaceutical composition of claim 4, wherein the anti-cancer agent is a therapeutic monoclonal antibody selected from anti-HER2/neu, anti-PD-1, anti-PD-L1, and anti-CTLA4.

6. The pharmaceutical composition of claim 5, further comprising epigallocatechin-3-O-gallate, wherein the anti-cancer agent is an anti-HER2/neu monoclonal antibody.

7. The pharmaceutical composition of claim 4, wherein the anti-cancer agent is doxorubicin, vincristine, vinorelbine, paclitaxel, or irinotecan.

8. The pharmaceutical composition of claim 2, wherein the anti-cancer agent includes a radioisotope.

9. The pharmaceutical composition of claim 8, wherein the radioisotope is $^{90}$Y, $^{125}$I, $^{68}$Ga, $^{188}$Re, $^{111}$In, or $^{131}$I.

10. A bispecific anti-cancer antibody, comprising the isolated cancer-targeting peptide of claim 1 and an antigen-binding peptide that stimulates T cell activity.

11. The bispecific anti-cancer antibody of claim 10, wherein the antigen is selected from the group consisting of CD3, PD-1, CTLA-4, LAG-3, TIM-3, TIGIT, VISTA, B7-H3, OX40, GITR, ICOS, and 41BB.

* * * * *

```
SEQUENCE LISTING

<160> NUMBER OF SEQ ID NOS: 15

<210> SEQ ID NO 1
<211> LENGTH: 4
<212> TYPE: PRT
<213> ORGANISM: Artificial Sequence
<220> FEATURE:
<223> OTHER INFORMATION: CTP repeat sequence 1

<400> SEQUENCE: 1

Pro Phe Leu Pro
1

<210> SEQ ID NO 2
<211> LENGTH: 4
<212> TYPE: PRT
<213> ORGANISM: Artificial Sequence
<220> FEATURE:
<223> OTHER INFORMATION: CTP repeat sequence 2

<400> SEQUENCE: 2

Pro Phe Leu Phe
1

<210> SEQ ID NO 3
<211> LENGTH: 12
<212> TYPE: PRT
<213> ORGANISM: Artificial Sequence
<220> FEATURE:
<223> OTHER INFORMATION: P6-CTP

<400> SEQUENCE: 3

Arg Leu Leu Asp Thr Asn Arg Pro Phe Leu Pro Tyr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: P13-CTP

<400> SEQUENCE: 4

Arg Leu Leu Asp Thr Asn Arg Pro Phe Leu Phe Tyr
1               5                   10

<210> SEQ ID NO 5
```

```
<211> LENGTH: 9
<212> TYPE: PRT
<213> ORGANISM: Artificial Sequence
<220> FEATURE:
<223> OTHER INFORMATION: F4P6-TR-CTP

<400> SEQUENCE: 5

Arg Pro Phe Leu Pro Phe Leu Pro Tyr
1               5

<210> SEQ ID NO 6
<211> LENGTH: 18
<212> TYPE: PRT
<213> ORGANISM: Artificial Sequence
<220> FEATURE:
<223> OTHER INFORMATION: F5P6-TR-CTP

<400> SEQUENCE: 6

Arg Pro Phe Leu Pro Phe Leu Pro Tyr Arg Pro Phe Leu Pro Phe Leu
1               5                   10                  15

Pro Tyr

<210> SEQ ID NO 7
<211> LENGTH: 10
<212> TYPE: PRT
<213> ORGANISM: Artificial Sequence
<220> FEATURE:
<223> OTHER INFORMATION: F4P13-TR-CTP

<400> SEQUENCE: 7

Arg Pro Phe Leu Phe Pro Phe Leu Phe Tyr
1               5                   10

<210> SEQ ID NO 8
<211> LENGTH: 20
<212> TYPE: PRT
<213> ORGANISM: Artificial Sequence
<220> FEATURE:
<223> OTHER INFORMATION: F5P13-TR-CTP

<400> SEQUENCE: 8

Arg Pro Phe Leu Phe Pro Phe Leu Phe Tyr Arg Pro Phe Leu Phe Pro
1               5                   10                  15

Phe Leu Phe Tyr
            20

<210> SEQ ID NO 9
<211> LENGTH: 5
<212> TYPE: PRT
<213> ORGANISM: Artificial Sequence
<220> FEATURE:
<223> OTHER INFORMATION: Synthetic linker

<400> SEQUENCE: 9

Gly Gly Gly Gly Ser
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic linker

<400> SEQUENCE: 10

Gly Gly Gly Gly Ser Lys
```

<210> SEQ ID NO 11
<211> LENGTH: 1677
<212> TYPE: DNA
<213> ORGANISM: Artificial Sequence
<220> FEATURE:
<223> OTHER INFORMATION: Hole arm F4P6-BsAb
<220> FEATURE:
<221> NAME/KEY: CDS
<222> LOCATION: (1)..(1677)

<400> SEQUENCE: 11

```
atg ggc ggt agg cgt gta cgg tgg gag gtc tat ata agc aga gct ggg      48
Met Gly Gly Arg Arg Val Arg Trp Glu Val Tyr Ile Ser Arg Ala Gly
1               5                   10                  15 tac gtg aac cgt cag atc gcc tgg aga cgc cat cac aga tct gcc acc      96
Tyr Val Asn Arg Gln Ile Ala Trp Arg Arg His His Arg Ser Ala Thr
                20                  25                  30 atg ggt tgg agc ctc atc ttg ctc ttc ctt gtc gct gtt gct acg cgt     144
Met Gly Trp Ser Leu Ile Leu Leu Phe Leu Val Ala Val Ala Thr Arg
            35                  40                  45 gtc ctg tcc cag gtg cag ctg gtg cag agc ggc gct gaa gtg aag aaa     192
Val Leu Ser Gln Val Gln Leu Val Gln Ser Gly Ala Glu Val Lys Lys
        50                  55                  60 cct ggc gcc tcc gtg aag gtg tcc tgc aag gct tct ggc tac acc ttt     240
Pro Gly Ala Ser Val Lys Val Ser Cys Lys Ala Ser Gly Tyr Thr Phe
65                  70                  75                  80 acc cgg tac acc atg cat tgg gtg cga cag gct cca ggc cag ggg ctg     288
Thr Arg Tyr Thr Met His Trp Val Arg Gln Ala Pro Gly Gln Gly Leu
                85                  90                  95 gaa tgg att ggc tac atc aac ccc agc cgg ggc tac acc aac tac aat     336
Glu Trp Ile Gly Tyr Ile Asn Pro Ser Arg Gly Tyr Thr Asn Tyr Asn
            100                 105                 110 cag aag ttc aag gat aag gcc acc ctg acc acc gac aag tcc atc tcc     384
Gln Lys Phe Lys Asp Lys Ala Thr Leu Thr Thr Asp Lys Ser Ile Ser
        115                 120                 125 acc gcc tac atg gaa ctg tcc cgg ctg aga tcc gac gat acc gct gtg     432
Thr Ala Tyr Met Glu Leu Ser Arg Leu Arg Ser Asp Asp Thr Ala Val
    130                 135                 140 tac tac tgc gcc cgg tac tac gac gac cac tac acc ctg gac tac tgg     480
Tyr Tyr Cys Ala Arg Tyr Tyr Asp Asp His Tyr Thr Leu Asp Tyr Trp
145                 150                 155                 160 gga cag ggt act ctc gtg act gtg tca agt ggc ggc gga gga tct ggc     528
Gly Gln Gly Thr Leu Val Thr Val Ser Ser Gly Gly Gly Gly Ser Gly
                165                 170                 175 gga ggt gga agt ggc gga ggc ggt tct gaa atc gtg ctg aca cag agc     576
Gly Gly Gly Ser Gly Gly Gly Gly Ser Glu Ile Val Leu Thr Gln Ser
            180                 185                 190 ccc gcc acc ctg tca ctg tct cca ggc gag aga gct acc ctg agc tgc     624
Pro Ala Thr Leu Ser Leu Ser Pro Gly Glu Arg Ala Thr Leu Ser Cys
        195                 200                 205 tct gcc tcc tcc tcc gtg tct tac atg aac tgg tat cag cag aag ccc     672
Ser Ala Ser Ser Ser Val Ser Tyr Met Asn Trp Tyr Gln Gln Lys Pro
    210                 215                 220 ggc cag gcc ccc aga cgg tgg atc tac gat acc tcc aag ctg gcc tcc     720
Gly Gln Ala Pro Arg Arg Trp Ile Tyr Asp Thr Ser Lys Leu Ala Ser
225                 230                 235                 240 ggc atc cct gcc aga ttc tcc ggc tct ggc tcc ggc acc tcc tat acc     768
Gly Ile Pro Ala Arg Phe Ser Gly Ser Gly Ser Gly Thr Ser Tyr Thr
                245                 250                 255
```

| | |
|---|---|
| ctg aca atc tcc agc ctg gaa ccc gag gac ttt gcc gtg tat tac tgc<br>Leu Thr Ile Ser Ser Leu Glu Pro Glu Asp Phe Ala Val Tyr Tyr Cys<br>260 265 270 | 816 |
| cag cag tgg tcc tcc aac ccc ttc acc ttc gga cag gga aca aag gtg<br>Gln Gln Trp Ser Ser Asn Pro Phe Thr Phe Gly Gln Gly Thr Lys Val<br>275 280 285 | 864 |
| gaa atc aag cgc tcc gga ggc gga agc gga ggc gga ggt tca ggt<br>Glu Ile Lys Arg Ser Gly Gly Gly Ser Gly Gly Gly Gly Ser Gly<br>290 295 300 | 912 |
| ggc gga gga tca acc ggt acc cac acc tgt cct cca tgc cct gcc cct<br>Gly Gly Gly Ser Thr Gly Thr His Thr Cys Pro Pro Cys Pro Ala Pro<br>305 310 315 320 | 960 |
| gag ctg gcc ggc gcc ccc tcc gtg ttc ctg ttc cct cca aag cct aag<br>Glu Leu Ala Gly Ala Pro Ser Val Phe Leu Phe Pro Pro Lys Pro Lys<br>325 330 335 | 1008 |
| gac acc ctg atg atc tcc cgg acc cct gaa gtg acc tgc gtg gtg gtg<br>Asp Thr Leu Met Ile Ser Arg Thr Pro Glu Val Thr Cys Val Val Val<br>340 345 350 | 1056 |
| gac gtg tcc cac gag gac cct gaa gtg aag ttc aat tgg tac gtg gac<br>Asp Val Ser His Glu Asp Pro Glu Val Lys Phe Asn Trp Tyr Val Asp<br>355 360 365 | 1104 |
| ggc gtg gaa gtg cac aac gcc aag acc aag ccc aga gag gaa cag tac<br>Gly Val Glu Val His Asn Ala Lys Thr Lys Pro Arg Glu Glu Gln Tyr<br>370 375 380 | 1152 |
| aac tcc acc tac cgg gtg gtg tcc gtg ctg acc gtg ctg cac cag gat<br>Asn Ser Thr Tyr Arg Val Val Ser Val Leu Thr Val Leu His Gln Asp<br>385 390 395 400 | 1200 |
| tgg ctg aac ggc aaa gag tac aag tgc aag gtg tcc aac aag gcc ctg<br>Trp Leu Asn Gly Lys Glu Tyr Lys Cys Lys Val Ser Asn Lys Ala Leu<br>405 410 415 | 1248 |
| cct gcc ccc atc gaa aag acc atc tcc aag gcc aag ggc cag cct cgg<br>Pro Ala Pro Ile Glu Lys Thr Ile Ser Lys Ala Lys Gly Gln Pro Arg<br>420 425 430 | 1296 |
| gaa cct caa gtg tgc acc ctg ccc cct agc cgg gaa gag atg acc aag<br>Glu Pro Gln Val Cys Thr Leu Pro Pro Ser Arg Glu Glu Met Thr Lys<br>435 440 445 | 1344 |
| aac cag gtg tcc ctg tcc tgc gcc gtg aag ggc ttc tac ccc tcc gac<br>Asn Gln Val Ser Leu Ser Cys Ala Val Lys Gly Phe Tyr Pro Ser Asp<br>450 455 460 | 1392 |
| att gcc gtg gaa tgg gag tcc aac ggc cag cct gag aac aac tac aag<br>Ile Ala Val Glu Trp Glu Ser Asn Gly Gln Pro Glu Asn Asn Tyr Lys<br>465 470 475 480 | 1440 |
| acc acc ccc cct gtg ctg gac tcc gac ggc tca ttc ttc ctg gtg tcc<br>Thr Thr Pro Pro Val Leu Asp Ser Asp Gly Ser Phe Phe Leu Val Ser<br>485 490 495 | 1488 |
| aag ctg aca gtg gac aag tcc cgg tgg cag cag ggc aac gtg ttc tcc<br>Lys Leu Thr Val Asp Lys Ser Arg Trp Gln Gln Gly Asn Val Phe Ser<br>500 505 510 | 1536 |
| tgc tcc gtg atg cac gag gcc ctg cac aac cac tac acc cag aag tcc<br>Cys Ser Val Met His Glu Ala Leu His Asn His Tyr Thr Gln Lys Ser<br>515 520 525 | 1584 |
| ctg agc ctg tcc ccc ggg aag ggc ggt ggt ggt tca ggc ggt ggc ggc<br>Leu Ser Leu Ser Pro Gly Lys Gly Gly Gly Gly Ser Gly Gly Gly Gly<br>530 535 540 | 1632 |
| agc ggc gga ggc gga tcc aga cca ttt ttg ccc ttt ctg ccc tac<br>Ser Gly Gly Gly Gly Ser Arg Pro Phe Leu Pro Phe Leu Pro Tyr<br>545 550 555 | 1677 |

<210> SEQ ID NO 12
<211> LENGTH: 559

<212> TYPE: PRT
<213> ORGANISM: Artificial Sequence
<220> FEATURE:
<223> OTHER INFORMATION: Synthetic Construct

<400> SEQUENCE: 12

```
Met Gly Gly Arg Arg Val Arg Trp Glu Val Tyr Ile Ser Arg Ala Gly
1               5                   10                  15

Tyr Val Asn Arg Gln Ile Ala Trp Arg Arg His His Arg Ser Ala Thr
            20                  25                  30

Met Gly Trp Ser Leu Ile Leu Leu Phe Leu Val Ala Val Ala Thr Arg
        35                  40                  45

Val Leu Ser Gln Val Gln Leu Val Gln Ser Gly Ala Glu Val Lys Lys
    50                  55                  60

Pro Gly Ala Ser Val Lys Val Ser Cys Lys Ala Ser Gly Tyr Thr Phe
65                  70                  75                  80

Thr Arg Tyr Thr Met His Trp Val Arg Gln Ala Pro Gly Gln Gly Leu
                85                  90                  95

Glu Trp Ile Gly Tyr Ile Asn Pro Ser Arg Gly Tyr Thr Asn Tyr Asn
            100                 105                 110

Gln Lys Phe Lys Asp Lys Ala Thr Leu Thr Thr Asp Lys Ser Ile Ser
        115                 120                 125

Thr Ala Tyr Met Glu Leu Ser Arg Leu Arg Ser Asp Asp Thr Ala Val
    130                 135                 140

Tyr Tyr Cys Ala Arg Tyr Tyr Asp Asp His Tyr Thr Leu Asp Tyr Trp
145                 150                 155                 160

Gly Gln Gly Thr Leu Val Thr Val Ser Ser Gly Gly Gly Gly Ser Gly
                165                 170                 175

Gly Gly Gly Ser Gly Gly Gly Ser Glu Ile Val Leu Thr Gln Ser
            180                 185                 190

Pro Ala Thr Leu Ser Leu Ser Pro Gly Glu Arg Ala Thr Leu Ser Cys
        195                 200                 205

Ser Ala Ser Ser Ser Val Ser Tyr Met Asn Trp Tyr Gln Gln Lys Pro
    210                 215                 220

Gly Gln Ala Pro Arg Arg Trp Ile Tyr Asp Thr Ser Lys Leu Ala Ser
225                 230                 235                 240

Gly Ile Pro Ala Arg Phe Ser Gly Ser Gly Ser Gly Thr Ser Tyr Thr
                245                 250                 255

Leu Thr Ile Ser Ser Leu Glu Pro Glu Asp Phe Ala Val Tyr Tyr Cys
            260                 265                 270

Gln Gln Trp Ser Ser Asn Pro Phe Thr Phe Gly Gln Gly Thr Lys Val
        275                 280                 285

Glu Ile Lys Arg Ser Gly Gly Gly Gly Ser Gly Gly Gly Gly Ser Gly
    290                 295                 300

Gly Gly Ser Thr Gly Thr His Thr Cys Pro Pro Cys Pro Ala Pro
305                 310                 315                 320

Glu Leu Ala Gly Ala Pro Ser Val Phe Leu Phe Pro Pro Lys Pro Lys
                325                 330                 335

Asp Thr Leu Met Ile Ser Arg Thr Pro Glu Val Thr Cys Val Val Val
            340                 345                 350

Asp Val Ser His Glu Asp Pro Glu Val Lys Phe Asn Trp Tyr Val Asp
        355                 360                 365

Gly Val Glu Val His Asn Ala Lys Thr Lys Pro Arg Glu Glu Gln Tyr
    370                 375                 380
```

```
Asn Ser Thr Tyr Arg Val Val Ser Val Leu Thr Val Leu His Gln Asp
385                 390                 395                 400

Trp Leu Asn Gly Lys Glu Tyr Lys Cys Lys Val Ser Asn Lys Ala Leu
            405                 410                 415

Pro Ala Pro Ile Glu Lys Thr Ile Ser Lys Ala Lys Gly Gln Pro Arg
        420                 425                 430

Glu Pro Gln Val Cys Thr Leu Pro Pro Ser Arg Glu Glu Met Thr Lys
    435                 440                 445

Asn Gln Val Ser Leu Ser Cys Ala Val Lys Gly Phe Tyr Pro Ser Asp
    450                 455                 460

Ile Ala Val Glu Trp Glu Ser Asn Gly Gln Pro Glu Asn Asn Tyr Lys
465                 470                 475                 480

Thr Thr Pro Pro Val Leu Asp Ser Asp Gly Ser Phe Phe Leu Val Ser
            485                 490                 495

Lys Leu Thr Val Asp Lys Ser Arg Trp Gln Gln Gly Asn Val Phe Ser
                500                 505                 510

Cys Ser Val Met His Glu Ala Leu His Asn His Tyr Thr Gln Lys Ser
            515                 520                 525

Leu Ser Leu Ser Pro Gly Lys Gly Gly Gly Ser Gly Gly Gly Gly
    530                 535                 540

Ser Gly Gly Gly Gly Ser Arg Pro Phe Leu Pro Phe Leu Pro Tyr
545                 550                 555
```

<210> SEQ ID NO 13
<211> LENGTH: 906
<212> TYPE: DNA
<213> ORGANISM: Artificial Sequence
<220> FEATURE:
<223> OTHER INFORMATION: Knob arm F4P6-BsAb
<220> FEATURE:
<221> NAME/KEY: CDS
<222> LOCATION: (1)..(906)

<400> SEQUENCE: 13

```
atg ggc ggt agg cgt gta cgg tgg gag gtc tat ata agc aga gct ggg     48
Met Gly Gly Arg Arg Val Arg Trp Glu Val Tyr Ile Ser Arg Ala Gly
1               5                   10                  15 tac gtg aac cgt cag atc gcc tgg aga cgc cat cac aga tct gcc acc     96
Tyr Val Asn Arg Gln Ile Ala Trp Arg Arg His His Arg Ser Ala Thr
                20                  25                  30 atg ggt tgg agc ctc atc ttg ctc ttc ctt gtc gct gtt gct acg cgt    144
Met Gly Trp Ser Leu Ile Leu Leu Phe Leu Val Ala Val Ala Thr Arg
            35                  40                  45 gtc ctg tcc acc ggt acc cac acc tgt cct cca tgc cct gcc cct gag    192
Val Leu Ser Thr Gly Thr His Thr Cys Pro Pro Cys Pro Ala Pro Glu
50                  55                  60 ctg gcc ggc gcc ccc tcc gtg ttc ctg ttc cct cca aag cct aag gac    240
Leu Ala Gly Ala Pro Ser Val Phe Leu Phe Pro Pro Lys Pro Lys Asp
65                  70                  75                  80 acc ctg atg atc tcc cgg acc cct gaa gtg acc tgc gtg gtg gtg gac    288
Thr Leu Met Ile Ser Arg Thr Pro Glu Val Thr Cys Val Val Val Asp
                85                  90                  95 gtg tcc cac gag gac cct gaa gtg aag ttc aat tgg tac gtg gac ggc    336
Val Ser His Glu Asp Pro Glu Val Lys Phe Asn Trp Tyr Val Asp Gly
                100                 105                 110 gtg gaa gtg cac aac gcc aag acc aag ccc aga gag gaa cag tac aac    384
Val Glu Val His Asn Ala Lys Thr Lys Pro Arg Glu Glu Gln Tyr Asn
            115                 120                 125 tcc acc tac cgg gtg gtg tcc gtg ctg acc gtg ctg cac cag gat tgg    432
```

-continued

```
Ser Thr Tyr Arg Val Val Ser Val Leu Thr Val Leu His Gln Asp Trp
    130                 135                 140 ctg aac ggc aaa gag tac aag tgc aag gtg tcc aac aag gcc ctg cct      480
Leu Asn Gly Lys Glu Tyr Lys Cys Lys Val Ser Asn Lys Ala Leu Pro
145                 150                 155                 160 gcc ccc atc gaa aag acc atc tcc aag gcc aag ggc cag ccc cgc gaa      528
Ala Pro Ile Glu Lys Thr Ile Ser Lys Ala Lys Gly Gln Pro Arg Glu
                165                 170                 175 ccc cag gtg tac aca ctg ccc cct tgc cgg gaa gag atg acc aag aac      576
Pro Gln Val Tyr Thr Leu Pro Pro Cys Arg Glu Glu Met Thr Lys Asn
            180                 185                 190 cag gtg tcc ctg tgg tgc ctc gtg aag ggc ttc tac ccc tcc gac att      624
Gln Val Ser Leu Trp Cys Leu Val Lys Gly Phe Tyr Pro Ser Asp Ile
        195                 200                 205 gcc gtg gaa tgg gag tcc aac ggc cag cct gag aac aac tac aag acc      672
Ala Val Glu Trp Glu Ser Asn Gly Gln Pro Glu Asn Asn Tyr Lys Thr
    210                 215                 220 acc ccc cct gtg ctg gac tcc gac ggc tca ttc ttc ctg tac tcc aag      720
Thr Pro Pro Val Leu Asp Ser Asp Gly Ser Phe Phe Leu Tyr Ser Lys
225                 230                 235                 240 ctg aca gtg gac aag tcc cgg tgg cag cag ggc aac gtg ttc tcc tgc      768
Leu Thr Val Asp Lys Ser Arg Trp Gln Gln Gly Asn Val Phe Ser Cys
                245                 250                 255 tcc gtg atg cac gag gcc ctg cac aac cac tac acc cag aag tcc ctg      816
Ser Val Met His Glu Ala Leu His Asn His Tyr Thr Gln Lys Ser Leu
            260                 265                 270 agc ctg tcc ccc ggg aag ggc ggt ggt ggt tca ggc ggt ggc ggc agc      864
Ser Leu Ser Pro Gly Lys Gly Gly Gly Gly Ser Gly Gly Gly Gly Ser
        275                 280                 285 ggc gga ggc gga tcc aga cca ttt ttg ccc ttt ctg ccc tac              906
Gly Gly Gly Gly Ser Arg Pro Phe Leu Pro Phe Leu Pro Tyr
    290                 295                 300
```

<210> SEQ ID NO 14
<211> LENGTH: 302
<212> TYPE: PRT
<213> ORGANISM: Artificial Sequence
<220> FEATURE:
<223> OTHER INFORMATION: Synthetic Construct

<400> SEQUENCE: 14

```
Met Gly Gly Arg Arg Val Arg Trp Glu Val Tyr Ile Ser Arg Ala Gly
1               5                   10                  15

Tyr Val Asn Arg Gln Ile Ala Trp Arg Arg His His Arg Ser Ala Thr
            20                  25                  30

Met Gly Trp Ser Leu Ile Leu Leu Phe Leu Val Ala Val Ala Thr Arg
        35                  40                  45

Val Leu Ser Thr Gly Thr His Thr Cys Pro Pro Cys Pro Ala Pro Glu
    50                  55                  60

Leu Ala Gly Ala Pro Ser Val Phe Leu Phe Pro Pro Lys Pro Lys Asp
65                  70                  75                  80

Thr Leu Met Ile Ser Arg Thr Pro Glu Val Thr Cys Val Val Val Asp
                85                  90                  95

Val Ser His Glu Asp Pro Glu Val Lys Phe Asn Trp Tyr Val Asp Gly
            100                 105                 110

Val Glu Val His Asn Ala Lys Thr Lys Pro Arg Glu Glu Gln Tyr Asn
        115                 120                 125

Ser Thr Tyr Arg Val Val Ser Val Leu Thr Val Leu His Gln Asp Trp
    130                 135                 140
```

```
Leu Asn Gly Lys Glu Tyr Lys Cys Lys Val Ser Asn Lys Ala Leu Pro
145                 150                 155                 160

Ala Pro Ile Glu Lys Thr Ile Ser Lys Ala Lys Gly Gln Pro Arg Glu
                165                 170                 175

Pro Gln Val Tyr Thr Leu Pro Pro Cys Arg Glu Glu Met Thr Lys Asn
            180                 185                 190

Gln Val Ser Leu Trp Cys Leu Val Lys Gly Phe Tyr Pro Ser Asp Ile
            195                 200                 205

Ala Val Glu Trp Glu Ser Asn Gly Gln Pro Glu Asn Asn Tyr Lys Thr
        210                 215                 220

Thr Pro Pro Val Leu Asp Ser Asp Gly Ser Phe Phe Leu Tyr Ser Lys
225                 230                 235                 240

Leu Thr Val Asp Lys Ser Arg Trp Gln Gln Gly Asn Val Phe Ser Cys
                245                 250                 255

Ser Val Met His Glu Ala Leu His Asn His Tyr Thr Gln Lys Ser Leu
                260                 265                 270

Ser Leu Ser Pro Gly Lys Gly Gly Gly Ser Gly Gly Gly Gly Gly Ser
            275                 280                 285

Gly Gly Gly Gly Ser Arg Pro Phe Leu Pro Phe Leu Pro Tyr
        290                 295                 300

<210> SEQ ID NO 15
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 15

Arg Leu Leu Asp Thr
1               5
```